(12) United States Patent
Weidman et al.

(10) Patent No.: US 10,175,371 B2
(45) Date of Patent: *Jan. 8, 2019

(54) METHOD AND APPARATUS FOR NOISE CONTROL IN ULTRASONIC SENSORS

(71) Applicant: The Watt Stopper, Inc., Carlsbad, CA (US)

(72) Inventors: Louia Weidman, Carlsbad, CA (US); Aizhong Chen, Shanghai (CN); Chenghao Fan, Shanghai (CN)

(73) Assignee: The Watt Stopper, Inc., Carlsbad, CA (US)

( * ) Notice: Subject to any disclaimer, the term of this patent is extended or adjusted under 35 U.S.C. 154(b) by 148 days.

This patent is subject to a terminal disclaimer.

(21) Appl. No.: 15/238,153

(22) Filed: Aug. 16, 2016

(65) Prior Publication Data

US 2017/0038487 A1 Feb. 9, 2017

Related U.S. Application Data

(63) Continuation of application No. 14/215,700, filed on Mar. 17, 2014, now Pat. No. 9,417,347.

(60) Provisional application No. 61/794,694, filed on Mar. 15, 2013.

(51) Int. Cl.
| | | |
|---|---|---|
| *G01N 29/00* | (2006.01) |
| *G01V 1/24* | (2006.01) |
| *G01N 29/34* | (2006.01) |
| *G01S 7/52* | (2006.01) |
| *G01S 15/04* | (2006.01) |
| *G01V 1/00* | (2006.01) |
| *H05B 37/02* | (2006.01) |
| *G01V 1/38* | (2006.01) |

(52) U.S. Cl.
CPC ............. *G01V 1/001* (2013.01); *G01N 29/34* (2013.01); *G01S 7/52004* (2013.01); *G01S 15/04* (2013.01); *G01V 1/247* (2013.01); *G01V 1/3852* (2013.01); *H05B 37/0227* (2013.01)

(58) Field of Classification Search
CPC ........ G01N 29/34; G01V 1/001; G01V 1/247; G01V 1/3852; G01S 15/04; G01S 7/52004
See application file for complete search history.

(56) References Cited

U.S. PATENT DOCUMENTS 9,417,347 B2 * 8/2016 Weidman ............... G01V 1/247

* cited by examiner

*Primary Examiner* — Helen Kwok
(74) *Attorney, Agent, or Firm* — K. David Crockett, Esq.; Paul J. Backofen, Esq.; Crockett & Crockett, PC

(57) ABSTRACT

The adjustable voltage regulator under control of a microcontroller applies controlled amplitude voltage in the range of 5 to 9 VDC to the sensor transmitter to adjust the output amplitude of the transmitter. The adjustable amplitude transmitter allows an occupancy sensor to have its total output energy adjusted to reduce environmental noise-induced false triggering and to conform to the area to be covered. Lowering the total ultrasonic energy in the monitored space lowers the sensitivity of the receiver to inappropriate activations. Lowering the input power to the transmitter also lowers the total internal system noise and provides an improved signal to noise ratio in the receiver.

1 Claim, 4 Drawing Sheets

METHOD AND APPARATUS FOR NOISE CONTROL IN ULTRASONIC SENSORS

RELATED APPLICATIONS

This application claims priority to copending U.S. Utility application Ser. No. 14/215,700 filed Mar. 17, 2014, now U.S. Pat. No. 9,417,347 which claims priority to U.S. Provisional Patent application 61/794,694 filed Mar. 15, 2013.

FIELD OF THE INVENTIONS

The inventions described below relate to the field of electrical controls and more specifically, sensors for automatically controlling electrical loads such as lighting.

BACKGROUND OF THE INVENTIONS

Active ultrasonic room occupancy sensors are equipped with an ultrasonic transmitter having an output with a generally fixed amplitude. Ultrasonic occupancy sensors are sensitive to environmental noise such as forced air, e.g, from a HVAC vent, and other extraneous air pressure changes that may be interpreted by the ultrasonic receiver as a return ultrasonic signal representing an occupancy state. This type of environmental noise may cause a false trigger, as is known in the art, causing the controlled load to change state unintentionally. Typically, the false trigger noise is interpreted as occupancy, causing the controlled load to turn on and waste energy when there is no one in the monitored space.

SUMMARY

The devices and methods described below provide for methods and apparatus for reducing environmental noise-induced false triggering in ultrasonic occupancy sensors by analyzing the signal from an ultrasonic peak voltage detector circuit to determine an average signal level that is used to automatically adjust the ultrasonic sensitivity level, as well as to determine the difference in ultrasonic peak voltages over time to determine occupancy.

The adjustable voltage regulator under control of a microcontroller applies controlled amplitude voltage in the range of 5 to 9 VDC to the sensor transmitter to adjust the output amplitude of the transmitter. The adjustable amplitude transmitter allows an occupancy sensor to have its total output energy adjusted to reduce environmental noise-induced false triggering and to conform to the area to be covered. Lowering the total ultrasonic energy in the monitored space lowers the sensitivity of the receiver to inappropriate activations. Lowering the input power to the transmitter also lowers the total internal system noise and provides an improved signal to noise ratio in the receiver.

DETAILED DESCRIPTION OF THE INVENTIONS

Figure 1:
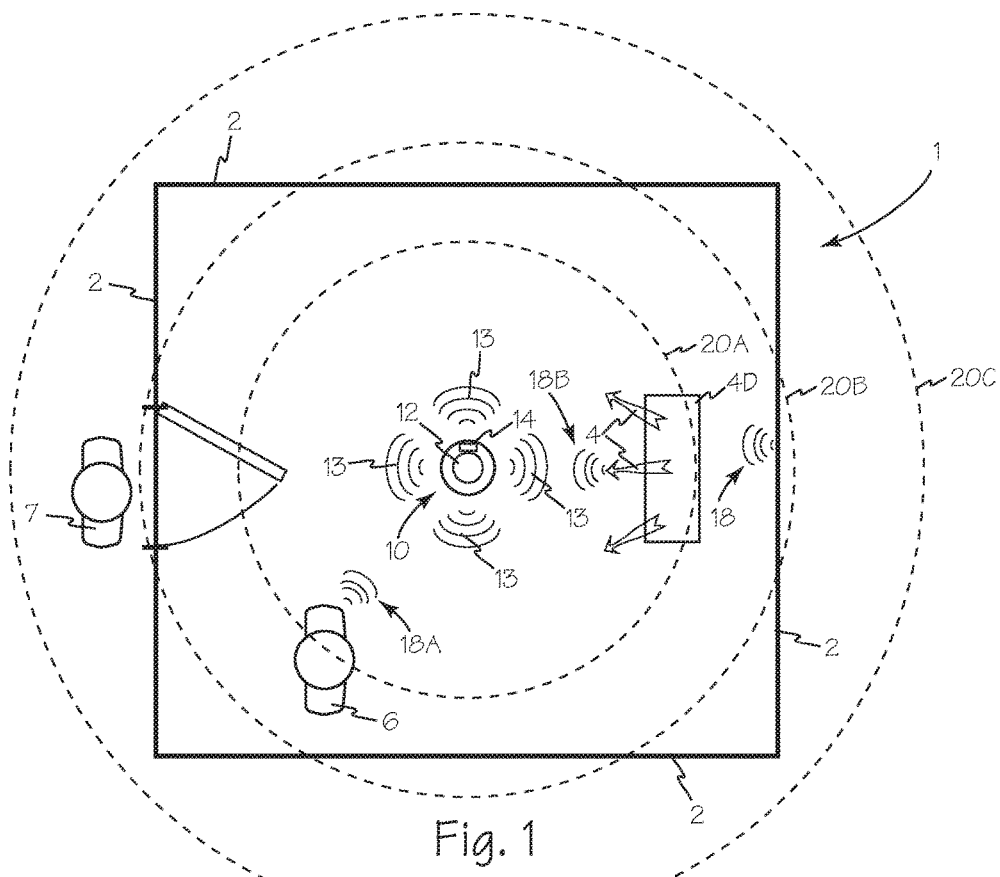
FIG. 1 is a top view of a room equipped with an adjustable amplitude active ultrasonic occupancy sensor.
Figure 2:
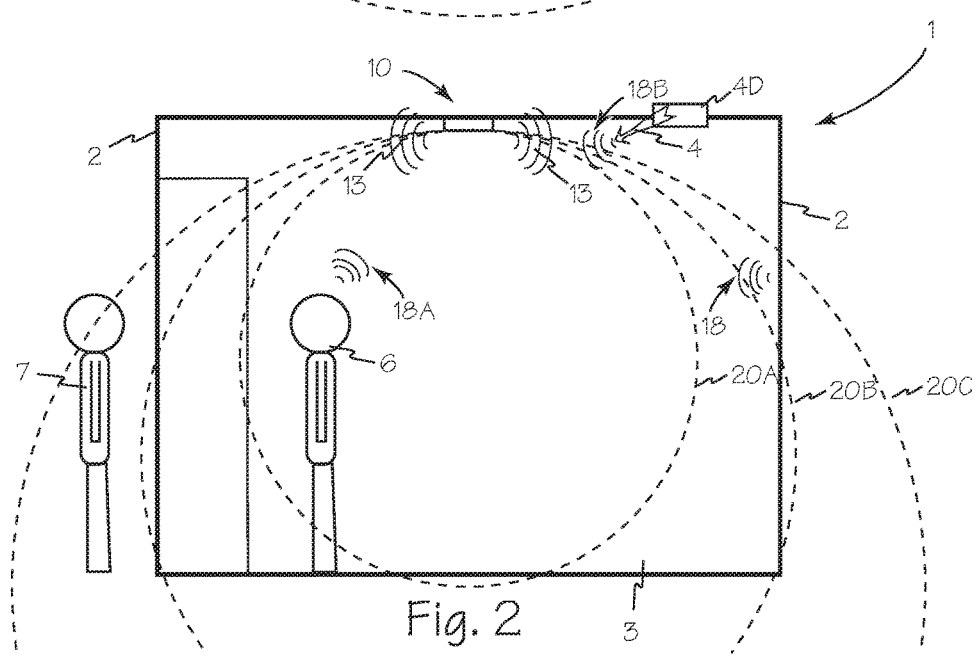
FIG. 2 is a side view of the room of FIG. 1.
Figure 3:
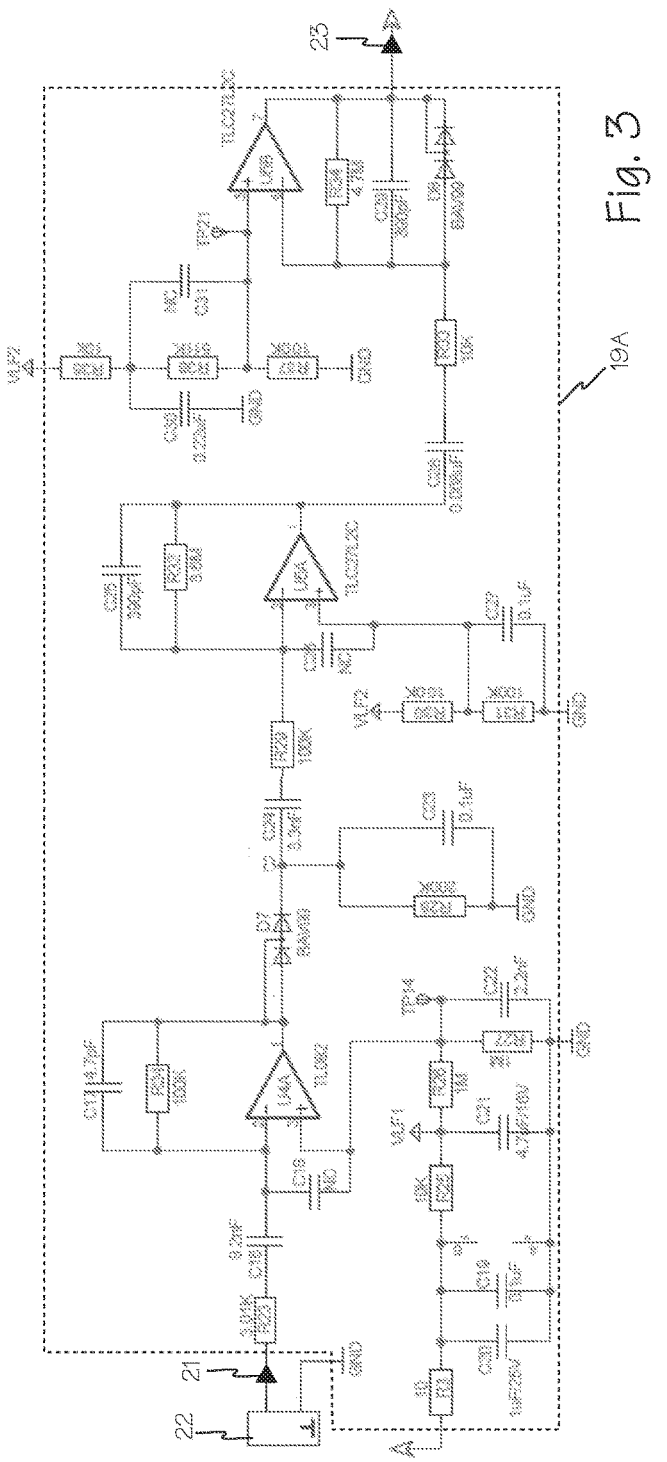
FIG. 3 is a schematic diagram of the receiver and amplifier circuit of the adjustable amplitude active ultrasonic occupancy sensor of FIG. 1.
Figure 4:
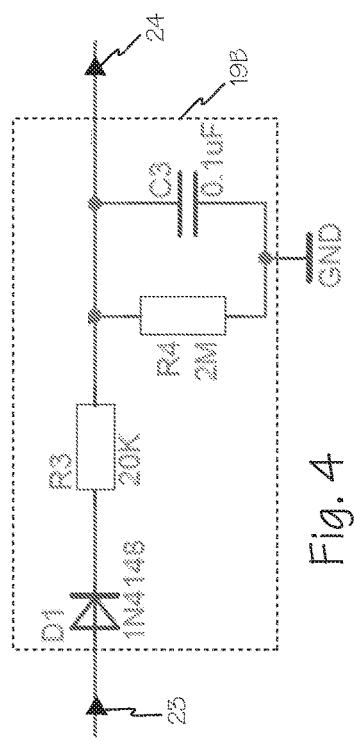
FIG. 4 is a schematic diagram of the noise signal generation circuit or peak detector circuit of the adjustable amplitude active ultrasonic occupancy sensor of FIG. 1.
Figure 5:
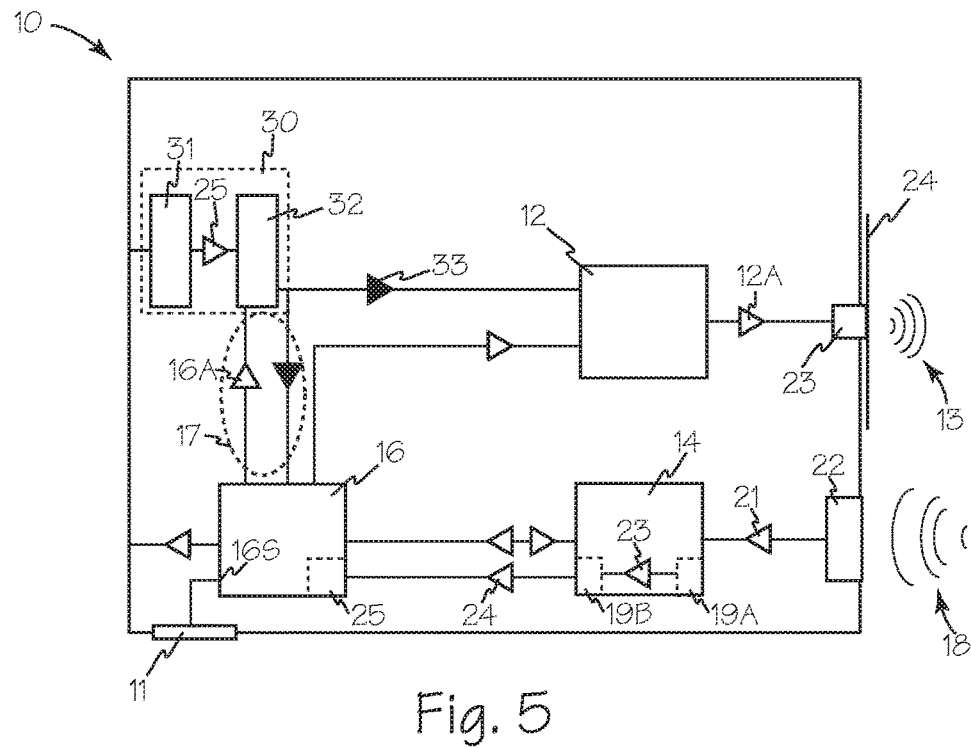
FIG. 5 is a block diagram of adjustable amplitude active ultrasonic occupancy sensor.

FIG. 1 is a top view, and FIG. 2 is a side view of room 1 equipped with adjustable amplitude active ultrasonic occupancy sensor 10 which is illustrated in FIG. 5. Sensor 10 includes a transmitter 12 and a receiver 14 which receives energy from power supply 30. Operation of transmitter 12, receiver 14 and power supply 30 are all controlled by microprocessor or controller 16. Transmitter 12 continuously transmits ultrasonic energy 13 into room 1. Ultrasonic energy 13 is reflected as incoming energy 18 by anything occupying room 1 including walls 2 floor 3 and as environmental signal 18B when reflected by transient environmental elements such as HVAC air 4. The amplitude of power applied to transmitter 12 can be adjusted to control the amplitude of ultrasonic output signal 13 and thus, the amplitude of reflected signals from the contents of the room, such as reflected signals 18, or the environmental elements of the room such as reflected signal 18B. The amplitude of output energy 13 is set such that reflected signals 18 from the edges of a desired zone of sensitivity such as zones 20A, 20B and 20C are at or below the noise threshold of receiver 14.

Amplifier filter circuit 19A processes raw input signal 21 from ultrasonic transducer 22 to produce signal 23 that represents the amplitude of the incoming ultrasonic envelope. Signal 23 is applied to peak detector 19B to generate ultrasonic peak noise signal 24 which is applied to controller 16. Ultrasonic peak noise signal 24 is used by sensitivity and threshold adjustment firmware 25.

Figure 6:
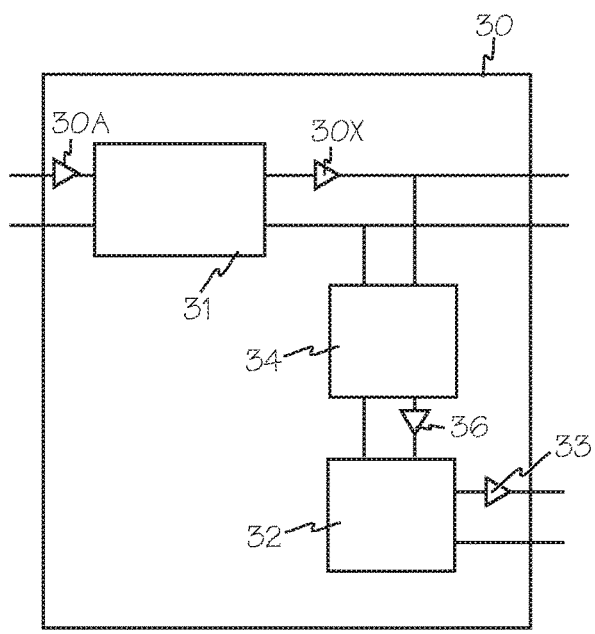
FIG. 6 is a block diagram of a power supply for an active ultrasonic occupancy sensor.

In use, the sensitivity of sensor 10 is a function of the regulated output of power supply 30 of FIGS. 5 and 6. Transmitter 12 operates as an ultrasonic oscillator under control of controller 16, powered by power supply 30. Output signal 12A is conveyed to transmitter crystal 26 which is mechanically connected to output plate 27. The vibrations of crystal 26 cause output plate 27 to vibrate and create transmitter signals such as ultrasound energy 16 which is transmitted to the space to be monitored such as room 1.

Power supply 30 includes main power supply 31 which processes input power 30A and produces main output power 30X. Power supply includes adjustable voltage regulator 32 which may be controlled by any sensor microcontroller such as controller 16 to produce regulated, controlled output power 33. Power supply 30 also includes fixed voltage regulator 34 which receives main output power 30X, transforms it into intermediate power 35, and applies intermediate power 35 to adjustable voltage regulator 32. Intermediate power 35 may have any suitable voltage between the voltage of main output power 30X and the voltage of regulated, controlled power 33. Main output power 30X is generally about 24 VDC, intermediate power is generally about 12 VDC and regulated, controlled output power 33 is generally in the range of 5-9 VDC. Other suitable voltages and voltage ranges may also be used. Output power 33 may also be applied to controller 16 to create feedback loop 17 to enable accurate control of the power applied to the transmitter while main power supply 31 may be an inexpensive, loosely regulate supply.

In a room such as room 1 equipped with adjustable amplitude active ultrasonic occupancy sensor 10, the amplitude of transmitter 12 can be adjusted such that the amplitude of signals 18A reflected by room occupant 6 are measurable and little or no ultrasonic energy is reflected from anyone or anything, such as non-occupant 7, outside the established sensitivity zone such as sensitivity zone 20B.

Sensitivity and threshold adjustment firmware 25 operates in two modes, Automatic mode 38 and Normal mode 39 using sensitivity and threshold adjustment method 40, based on the value of the ultrasonic peak noise signal 24. The sensitivity adjustment of ultrasonic occupancy sensors such as sensor 10 may be set manually on the device using sensitivity control 11 which may be any suitable interface such as a trimming potentiometer or via pushbuttons under firmware control, or via a commissioning tool that is in communication with the sensor (e.g., network cable, wireless, etc.).

When the ultrasonic sensitivity input 16S is set to 0%, sensor 10 enters the Automatic mode; a setting other than 0% at ultrasonic sensitivity input 16S causes the sensor to operate in Normal mode. Automatic mode operates to establish sensitivity and threshold values and can periodically adjust the sensitivity according to environmental noise levels. Normal mode is the normal occupancy sensing mode that also includes sensitivity adjustment capability as noted above.

Figure 7:
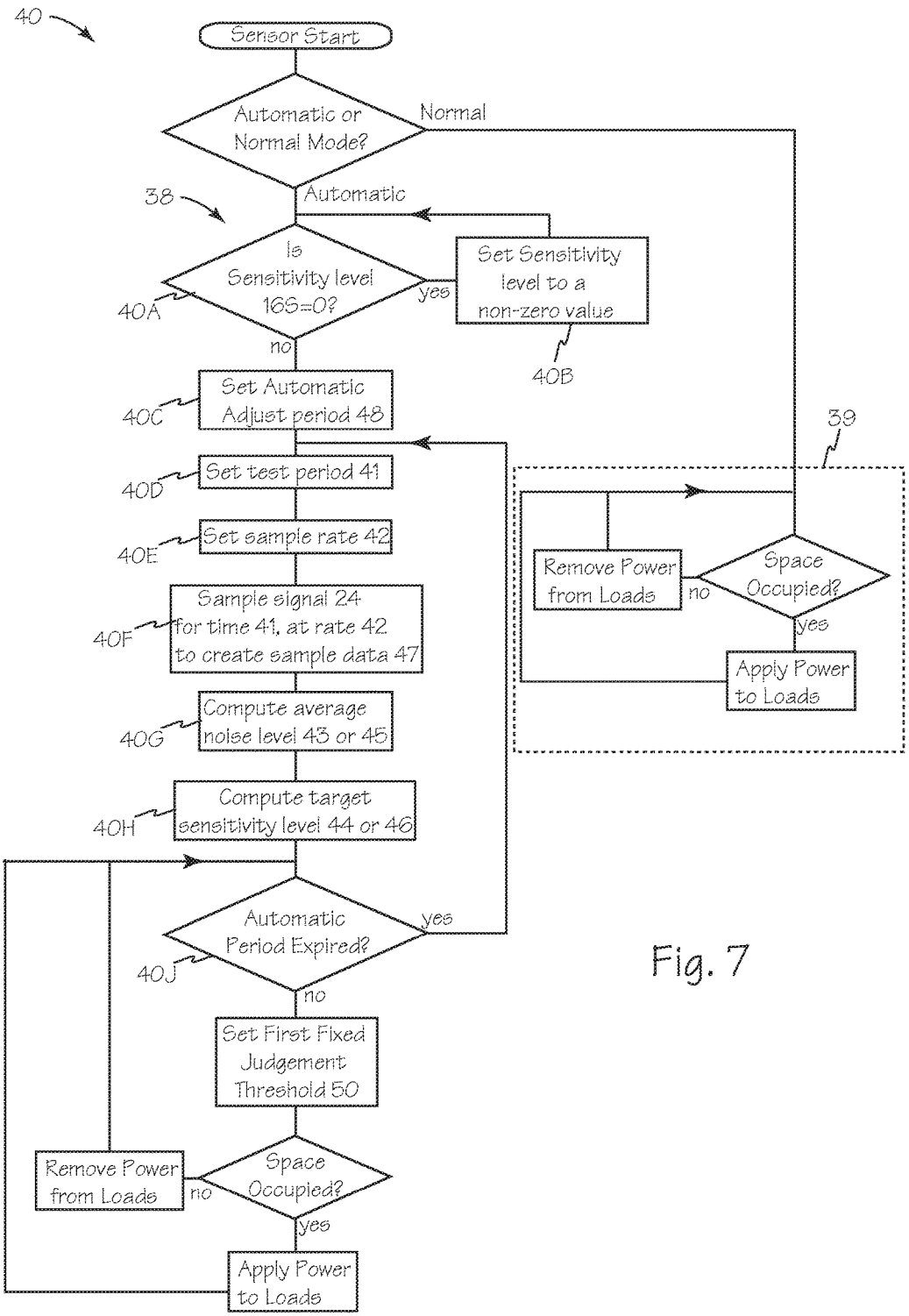
FIG. 7 is a flow chart of the operating algorithm of the occupancy sensor.

Referring now to FIG. 7, there are two phases to Automatic mode, P1 and P2. Phase P1 occurs at step 40A when controller 16 determines that it is the first time sensor 10 has been powered or when sensitivity input 16S has an input value equal to zero. A baseline sensitivity value is set at step 40B by first setting the ultrasonic sensitivity to a starting value, e.g., 41%. Then at step 40C, automatic adjust time period 48 is set and at step 40D test time 41 is set to any suitable period, at step 40E sample rate 42 is set to a suitable sampling rate. At step 40F peak ultrasonic signal, signal 24 is sampled for test period 41 at sampling rate 42 to create sample data 47. Sample rate 42 is set to any suitable rate such as of 16.67 millisecond per sample. Sample rate 42 is simply any suitable and convenient rate and not Nyquist sampling theorem related. The intent of the sampling rate is to get a sufficient number of samples within a short enough period of time to assess whether or not the noise signal is related to a human occupant or an environmental noise source. At step 40G the sampled peak ultrasonic signal values are then averaged to create an average noise level 43. The average noise level 43 is used at step 40H to determine a target ultrasonic sensitivity level 44 based on empirical data; generally, a higher average value results in a smaller target sensitivity level and visa-versa.

For example, an experiment can be set up in room 1 to create different levels of environmental noise, such as airflow 4 from HVAC air duct 4D for a ceiling mounted occupancy sensor, and adjust the sensitivity level until environmental-noise-induced false triggering stops. A table of noise levels and associated sensitivity levels needed to accommodate the environmental noise can be created and implemented in threshold adjustment firmware 25. The working ultrasonic sensitivity value, used during normal operation, is set to the target ultrasonic sensitivity level 44. The target ultrasonic sensitivity value is also saved in a variable that stores the old ultrasonic sensitivity value to establish a beginning value for that variable for future operation.

In its second phase, phase P2, Automatic mode is periodically run according to automatic adjust period 48 to adjust sensitivity level 44. Phase P2 starts once phase P1 is completed. At the current working sensitivity level, level 44, the peak ultrasonic signal 24 is sampled at step 40F and averaged over any suitable sample period as discussed in P1 create a P2 average noise level 45. During signal sampling, signal 24 is also evaluated for occupancy. At the end of the sampling interval at step 40H, the P2 target sensitivity level 46 is set to a value corresponding to the new average noise level.

In phase P2, sample data 47 are analyzed to determine the difference between the maximum and minimum signal values within the sampling interval. If this difference is greater than a first fixed judgement threshold 50, the noise source is considered human and sensitivity is not adjusted (e.g., a person is moving around the monitored space). First fixed judgement threshold 50 is determined experimentally by comparing sampling interval data with human movement present to data with only environmental noise and is generally a fixed value. However, a user or a service technician may be given access to adjusting this fixed value using a suitable commissioning method or tool. If the voltage difference between the maximum and minimum voltages within the sampling interval are less than or equal to the first fixed judgement threshold, the noise source is considered environmental. In that case, the sensitivity level is adjusted to a value to prevent false triggering.

Additional analysis may be done to determine if the sensitivity adjustment should be done quickly to handle a sudden change in environmental noise or slowly to handle a more subtle change in environmental noise. In this additional analysis, the scale of the difference is determined by comparing the target sensitivity level to a comparison sensitivity level that is twice the sum of the old ultrasonic sensitivity to get a determination of relative change in noise level. A margin sensitivity value may be added to this sum to provide additional allowance for sensor operating factors (transducer performance, gain and filter values, etc.) where the margin sensitivity value is determined experimentally. If the target sensitivity is greater than the comparison sensitivity level, then a quick sensitivity adjustment is done consisting of storing the working ultrasonic sensitivity level to the old ultrasonic sensitivity variable and then making the working ultrasonic sensitivity the same as the target sensitivity level. If the target sensitivity level is less than or equal to the comparison sensitivity level, then a slow sensitivity adjustment is done consisting of adjusting the working sensitivity level toward the target sensitivity level in steps (plus or minus) that are 10% of the the difference where the step change is done every 2 seconds; this allows the sensitivity level to still be checked during the adjustment period dynamically.

In Normal mode (and in both phases of Automatic mode), the sensor determines when a detection event occurs and attempts to determine the source of the event, human or environment noise. The ultrasound peak detect signal 24 is sampled at a suitable and convenient interval as discussed above. For example, samples may be taken for approximately 200 milliseconds (12 samples), which provides a reasonable trade-off between accuracy and response time. Accuracy can be improved by taking more samples, e.g., over 1 second, but then a person entering a monitored space will notice a distinct delay before the controlled lighting load is turned on. A user acceptable response time is generally under 1 second, and more typically under 0.5 seconds.

The samples are then analyzed to determine the voltage difference between the maximum and minimum voltages within the sample period. The voltage difference is compared to a second fixed threshold difference value. The second fixed judgement threshold is determined experimentally by comparing 2-millisecond-interval data from human movement to that from environmental noise and is generally a fixed value; however, the user or a service technician may be given access to adjusting this fixed value using a suitable commissioning method or tool. If the voltage difference is greater than the second fixed threshold difference value, the signal is interpreted as human motion and the controlled lighting load is turn on (if not already on). If the voltage difference is less than or equal to the second fixed threshold difference value, the signal is interpreted as a noise source and is ignored.

In addition to adjusting the power to the transmitter, the amplitude of the power applied to receiver 19 can be adjusted to control the sensitivity of the receiver. Controlling the amplitude of the power applied to the receiver lowers the noise input to the receiver improving the receiver's efficiency. With this configuration, a measurable disturbance of reflected energy 18 will result in a change in measurable input signal 21 at receiver 14 thus permitting the amplitude of power applied to receiver 14 to control the level of movement or activity detected within the sensitivity zone, such as zone 20B, that triggers sensor 10.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method of operating an active ultrasonic occupancy sensor comprising the steps:
 providing an ultrasonic occupancy sensor comprising:
  an ultrasonic transmitter;
  an ultrasonic receiver;
  a power supply configured to apply power to an adjustable voltage regulator which is configured to apply adjustable power to the ultrasonic transmitter;
  a microcontroller; and
  a peak detector;
 processing a received ultrasonic signal to generate a first signal representing an ultrasonic voltage envelope;
 processing the first signal to generate an ultrasonic peak noise signal; and
 controlling the adjustable power of the adjustable voltage regulator according to the ultrasonic peak noise signal.

* * * * *